(12) United States Patent
Nikawa

(10) Patent No.: US 8,859,009 B2
(45) Date of Patent: Oct. 14, 2014

(54) METHOD OF FIXING ANTIBACTERIAL AGENT AND ARTICLE OBTAINED BY THE METHOD

(75) Inventor: Hiroki Nikawa, Hiroshima (JP)

(73) Assignee: Hiroshima University (JP)

( * ) Notice: Subject to any disclaimer, the term of this patent is extended or adjusted under 35 U.S.C. 154(b) by 668 days.

(21) Appl. No.: 12/736,794

(22) PCT Filed: Apr. 21, 2009

(86) PCT No.: PCT/JP2009/058229
§ 371 (c)(1),
(2), (4) Date: Feb. 9, 2011

(87) PCT Pub. No.: WO2009/136561
PCT Pub. Date: Nov. 12, 2009

(65) Prior Publication Data
US 2011/0172183 A1 Jul. 14, 2011

(30) Foreign Application Priority Data
May 9, 2008 (JP) .................. 2008-123450

(51) Int. Cl.
*A61K 33/40* (2006.01)

(52) U.S. Cl.
USPC ............ 424/613; 424/405; 427/452; 510/384

(58) Field of Classification Search
USPC ............... 424/613, 405; 427/452; 510/384
See application file for complete search history.

(56) References Cited

U.S. PATENT DOCUMENTS

| | | | | |
|---|---|---|---|---|
| 3,836,669 | A | * | 9/1974 | Dadekian ................. 514/642 |
| 7,811,453 | B2 | * | 10/2010 | Yotani et al. .............. 210/198.2 |
| 2006/0134163 | A1 | * | 6/2006 | Bagwell et al. ............. 424/422 |
| 2007/0065475 | A1 | * | 3/2007 | Elfersy ................... 424/405 |

FOREIGN PATENT DOCUMENTS

| | | |
|---|---|---|
| EP | 1 094 090 A2 | 4/2001 |
| JP | 62-048601 | 3/1987 |
| JP | 11-246310 | 9/1999 |
| JP | 2000-290405 A | 10/2000 |
| JP | 2001-288062 | 10/2001 |
| JP | 2001-329088 A | 11/2001 |
| JP | 2003-145669 | 5/2003 |
| JP | 2004-209241 | 7/2004 |
| JP | A-2007-125548 | 5/2007 |
| JP | A-2007-126557 | 5/2007 |
| JP | 2007-146134 | 6/2007 |
| WO | WO 99/56714 | 11/1999 |
| WO | WO 02/100455 A2 | 12/2002 |
| WO | WO 2007/031775 | 3/2007 |
| WO | WO 2007/063701 A1 | 6/2007 |

OTHER PUBLICATIONS

International Search Report for International Application No. PCT/JP2009/058229 mailed Jun. 2, 2009.

Nikawa. "Hoteibutsu no Kokin Coat-zai Nikabaiogado—sono Koka to Tokucho ni Tsuite." *Nippon Dental Review*. vol. 66. No. 10. Oct. 11, 2006. pp. 103-110.—English Translation Provided.
Office Action for Chinese Patent Application No. 2009801270768 mailed Dec. 4, 2012.
Chinese Office Action for corresponding Chinese Patent Application No. 200980127076.8 (mailed Aug. 6, 2013).
European Search Report for EP 09742685.2 (mailed Jul. 30, 2013), 10 pp.
Isquith et al. "Surface-Bonded Antimicrobial Activity of an Organosilicon Quaternary Ammonium Chloride," *Applied Microbiology*, 24(6):859-863 (1972).
Walters et al. "Algicidal Activity of a Surface-Bonded Organosilicon Quaternary Ammonium Chloride," *Applied Microbiology*, 25(2):253-256 (1973).
Japanese Office Action for corresponding Japanese Patent Application No. 2010-511046 (mailed Oct. 2, 2013).
Chinese Office Action for corresponding Chinese Patent Application No. 200980127076.8 (mailed Apr. 3, 2014).
Japanese Office Action for corresponding Japanese Patent Application No. 2010-511046 (mailed Jun. 24, 2014).

* cited by examiner

*Primary Examiner* — Renee Claytor
*Assistant Examiner* — Shobha Kantamneni
(74) *Attorney, Agent, or Firm* — Merchant & Gould P.C.

(57) ABSTRACT

An object of the present invention is to provide a method of fixing an antibacterial agent, by which method it is possible to impart articles of a wide range of materials with excellent antibacterial property and good persistence of antibacterial activity. Specifically, the method of fixing an antibacterial agent, comprises the steps of:
  subjecting a surface of an article to a surface treatment of providing the surface with oxygen-containing functional groups; and then
  subjecting the article to a treatment using an antibacterial agent composition including a silicon-containing compound (a) represented by general formula (1) below.

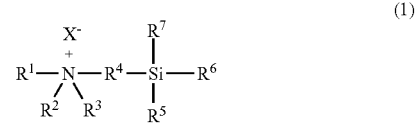

(1)

wherein $R^1$ represents a hydrocarbon group having 6 or more carbon atoms, $R^2$ and $R^3$ represent lower hydrocarbon groups, respectively, which hydrocarbon groups may be the same or different from each other, $R^4$ represents a divalent lower hydrocarbon group, $R^5$, $R^6$ and $R^7$ represent lower alkyl groups or lower alkoxy groups, respectively, which may be the same or different from each other, and X represents a halogen ion or an organic carbonyloxy ion, or alternatively, first treating the article by using the antibacterial agent composition; and then subjecting the article to a 1-10 GHz microwave irradiation treatment in a state where the antibacterial agent composition remains on the surface of the article.

6 Claims, 5 Drawing Sheets
(5 of 5 Drawing Sheet(s) Filed in Color)

METHOD OF FIXING ANTIBACTERIAL AGENT AND ARTICLE OBTAINED BY THE METHOD

This application is a National Stage Application of PCT/JP2009/058229, filed 21 Apr. 2009, which claims benefit of Serial No. 2008-123450, filed 9 May 2008 in Japan and which applications are incorporated herein by reference. To the extent appropriate, a claim of priority is made to each of the above disclosed applications.

TECHNICAL FIELD

The present invention relates to a method of fixing an antibacterial agent, by which not only excellent antibacterial properties and good persistence of antibacterial effect but also excellent cleaning properties can be imparted to an article. The present invention also relates to an article obtained by the method of fixing an antibacterial agent.

PRIOR ART

As population of our society is aging, the number of people using dental materials, in particular, dentures is increasing and an amount of use of denture cleaners is increasing accordingly. Currently, denture cleaners of various compositions are being used. Further, as people's concern over hygiene of daily-life environment increases, there is increasingly a demand for higher hygienic and antibacterial standards for tableware, eyeglasses, sinks, kitchen fixtures, toilets, toilet fixtures, bathtubs, bath-room fixtures, washbowls, washroom fixtures, textile products and clothes.

Compositions of the antibacterial agents used in the aforementioned articles can be classified, according to component systems, into those containing as a main component one of peroxide, Hypochlorous acid, enzymes, acids, herbal medicines, and silver-based inorganic antibacterial agent/disinfectant or those containing at least two types of these components in combination. Compositions of the antibacterial agent, if they belong to the same category of the aforementioned component systems, vary from each other in specific compositions thereof.

Various types of antibacterial agent compositions are used as described above because both cleaning performance and antiseptic performance are required of the composition of an antibacterial agent when the antibacterial agent is used as a denture cleanser, in particular. Composition of such an antibacterial agent as described above is thus generally constituted of components exhibiting the respective (cleaning and antiseptic) effects in combination.

In view of the requirement as described above, WO 99/56714 A1 discloses, to address a problem that a good cleaning and foaming effect of sodium lauryl sulfate tends to be decreased due to other components combined therewith in the conventional denture cleanser, a denture cleanser containing sodium lauryl sulfate and antibacterial metal ions such as silver, cupper, zinc ions and capable of further improving antiseptic performance without disturbing the function of sodium lauryl sulfate.

Further, there is a problem in the prior art that, although an acidic denture (artificial tooth) cleaner is preferable for removal of denture plaque, most of denture cleaners are adjusted to exhibit neutral pH, thereby inevitably decreasing cleaning performance thereof, because an acidic denture cleaner causes a gum material to be deformed and/or discolored and a metal material to be blackened. To address this problem, JP 2001-288062 discloses a granular or tablet-like denture cleaner comprising an acidic rapidly dissolving part containing an acid and a persulfate and an alkaline slowly dissolving part containing a carbonate and a perborate and/or a percarbonate, wherein, when the artificial tooth cleaner is mixed with an artificial tooth cleaning water, the cleaner can change the liquid property of the cleaning water from a low pH to a high pH.

JP 2004-209241 discloses an antibacterial material having an antibacterial substance such as octadecyltrimethoxysilane, γ-aminopropyltriethoxysilane, octadecyldimethyl(3-trimethoxysilylpropyl)ammonium chloride immobilized at a surface thereof and also discloses that the antibacterial material can be used for dental applications such as artificial tooth, implant, crown, bridge, orthodontic bracket, wire and the like. However, JP 2004-209241 fails to disclose an antibacterial agent composition itself containing the aforementioned antibacterial components.

There have been available, due to the improvement of antibacterial agent compositions as described above, antibacterial agents possessing improved cleaning and antiseptic performances. However, in the case of the conventional antibacterial agent, there is a problem that, although dental materials such as artificial tooth, implant, crown, bridge, orthodontic bracket, and dental wire can be cleaned by using the antibacterial agent, the antibacterial agent cannot prevent denture plaque from being formed again at a surface of an artificial tooth during use of the artificial tooth fixed inside a mouth cavity. Further, there is a demand for an antibacterial agent possessing improved performance of cleaning dental materials, in particular, cleaning artificial teeth. Yet further, there is a demand for such improved antibacterial and cleaning performances and good persistence of antibacterial and cleaning activities in antibacterial agents for use in tableware, eyeglasses, sinks, kitchen fixtures, toilets, toilet fixtures, bathtubs, bath-room fixtures, washbowls, washroom fixtures, textile products and clothes.

In view of the problems described above, JP 2007-146134 aims at improving antibacterial and antiseptic performances of an antibacterial agent and also improving antibacterial and cleaning performances and persistence of antibacterial and cleaning activities of an article cleaned with the antibacterial cleaner. Specifically, JP 2007-146134 aims at providing a composition of antibacterial agent for dental materials such as implant, crown, bridge, orthodontic bracket and dental wire, in particular, an artificial tooth, the composition being excellent in both antibacterial and cleaning performances to enable preventing denture plaque from being formed at a surface of an artificial tooth during use of the artificial tooth fixed within a mouth cavity. JP 2007-146134 also aims at providing a composition of artificial tooth cleaner, which composition is capable of easily imparting an artificial tooth with antibacterial properties without causing a user of the artificial tooth to feel unpleasant and/or any specific burden.

Further, JP 2007-146134 aims at providing a composition of a cleaner for use in tableware, eyeglasses, sinks, kitchen fixtures, toilets, toilet fixtures, bathtubs, bath-room fixtures, washbowls, washroom fixtures, textile products and clothes, which composition can meet a demand for excellent antibacterial and cleaning performances and good persistence of antibacterial and cleaning activities in the aforementioned articles as in dental materials.

DISCLOSURE OF THE INVENTION

Problems to be Solved by the Invention

Due to increasing people's concern over hygiene of daily-life environment in recent years, there has been a demand, in cleaning articles of a wide range of materials by using an antibacterial cleaner, for imparting these articles with further better antibacterial property and good persistence of antibacterial activity. However, the silicon-containing compound included in the cleaner composition of JP 2007-146134 does not have, although the compound exhibits relatively high bonding capability to some materials like glass and ceramics, good bonding capability with respect to synthetic resins, whereby the ability of the compound of imparting synthetic resin-made articles with antibacterial property and good persistence of the antibacterial activity is not sufficient.

In view of the facts above, an object of the present invention is to provide a method of fixing an antibacterial agent, by which method it is possible to impart articles of a wide range of materials with excellent antibacterial property and good persistence of antibacterial activity. Specifically, a silicon-containing compound based antibacterial agent used in the present invention is most critically characterized in that the compound is fixed to a surface of an article to be treated by chemical bonding. Details of the mechanism will be described hereinbelow.

The chemical equation below shows an example of fixation by using a composition of antibacterial agent containing (a) octadecyldimethyl(3-triethoxysilylpropyl)ammonium chloride (EtAC) as one example of the silicon-containing compound for use in the present invention. When EtAC is coated on a surface of an article to be treated, the oxygen-containing functional groups (—OC$_2$H$_5$: ethoxy group) thereof which each function as a "foot" site during fixation of EtAC are reacted with oxygen-containing functional groups present on a surface of the article and covalent-bonded with the oxygen-containing functional groups by way of oxygen atoms, with releasing ethanol. As a result of this chemical reaction, antibacterially-active sites of the silicon-containing compound (a) are firmly fixed on the surface of the article and thus the surface of the treated article is imparted with sufficiently strong antibacterial property and good persistence of antibacterial activity.

EtAC:

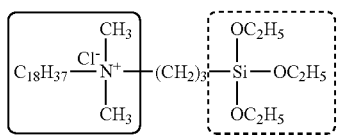

Antibacterially active site    Site functioning as "foot" during fixation

+

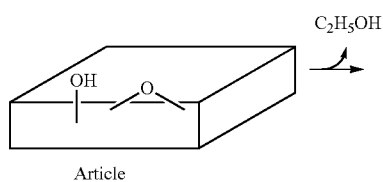

Article

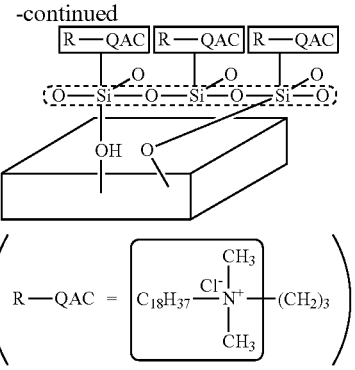

In a case of a synthetic resin such as polypropylene, polyethylene, acrylic resin and the like, where oxygen-containing functional groups do not exist or exist only by a relatively small percentage on a surface thereof, there arises a problem that the silicon-containing compound having antibacterial function fails to be fixed or is fixed but only by an extremely low fixation rate on a surface of an article to be treated and cannot function as a fixed antibacterial agent.

The inventors of the present invention discovered, as a result of a keen study to solve the aforementioned problems, that it is possible to impart an article made of synthetic resin with very good antibacterial property and good persistence of antibacterial activity by subjecting the article to a surface treatment of providing a surface of the article with oxygen-containing functional groups prior to subjecting the article to a treatment by using the aforementioned composition of antibacterial agent, thereby completing the present invention.

Specifically, a method of fixing an antibacterial agent of the present invention comprises the steps of:

subjecting a surface of an article to a surface treatment of providing the surface with oxygen-containing functional groups; and then subjecting the article to a treatment using an antibacterial agent composition including a silicon-containing compound (a) represented by general formula (1) below.

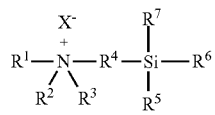

(1)

In general formula (1), $R^1$ represents a hydrocarbon group having 6 or more carbon atoms, $R^2$ and $R^3$ represent lower hydrocarbon groups, respectively, which hydrocarbon groups may be the same or different from each other, $R^4$ represents a divalent lower hydrocarbon group, $R^5$, $R^6$ and $R^7$ represent lower alkyl groups or lower alkoxy groups, respectively, which may be the same or different from each other, and X represents a halogen ion or an organic carbonyloxy ion.

The aforementioned surface treatment may be an ozone water treatment or a 1-10 GHz microwave irradiation treatment.

In another aspect of the present invention, a method of fixing an antibacterial agent comprises the steps of:

treating an article by using an antibacterial agent composition including a silicon-containing compound (a) represented by general formula (1) below; and then subjecting the article to a 1-10 GHz microwave irradiation treatment in a state where the antibacterial agent composition remains on a surface of the article.

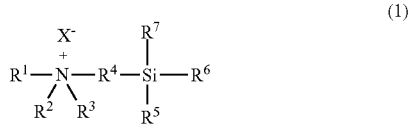

(1)

In general formula (1), $R^1$ represents a hydrocarbon group having 6 or more carbon atoms, $R^2$ and $R^3$ represent lower hydrocarbon groups, respectively, which hydrocarbon groups may be the same or different from each other, $R^4$ represents a divalent lower hydrocarbon group, $R^5$, $R^6$ and $R^7$ represent lower alkyl groups or lower alkoxy groups, respectively, which may be the same or different from each other, and X represents a halogen ion or an organic carbonyloxy ion.

In a preferable example of the method of fixing an antibacterial agent of the present invention, it is preferable that the composition of antibacterial agent includes (b) at least one type of surfactant selected from the group consisting of: (b1) cationic surfactant (note that the aforementioned silicon compound is to be excluded); (b2) non-ionic surfactant; and (b3) amphoteric surfactant.

In another preferable example of the method of fixing an antibacterial agent of the present invention, $R^1$ of the silicon-containing compound (a) represented by general formula (1) represents $C_{10-25}$ alkyl group, $R^2$ and $R^3$ represent $C_{1-6}$ lower alkyl groups, respectively, which alkyl groups may be the same or different from each other, $R^4$ represents a $C_{1-6}$ lower alkylene group, $R^5$, $R^6$ and $R^7$ represent $C_{1-6}$ lower alkyl groups or $C_{1-6}$ lower alkoxy groups, respectively, which may be the same or different from each other, and X represents a halogen ion or an organic carbonyloxy ion.

In yet another preferable example of the method of fixing an antibacterial agent of the present invention, the silicon-containing compound (a) represented by general formula (1) is preferably at least one type of silicon-containing compound selected from the group consisting of octadecyldimethyl(3-trimethoxysilylpropyl)ammonium chloride, octadecyldimethyl(3-triethoxysilylpropyl)ammonium chloride, octadecyldiethyl(3-trimethoxysilylpropyl)ammonium chloride, octadecyldimethyl(3-trimethylsilylethyl)ammonium chloride, octadecyldipropyl(4-timethoxysilylbutyl)ammonium acetate, octadecyldimethyl(3-triisopropoxysilylpropyl)ammonium chloride, octadecyldimethyl(3-triethylsilylpropyl) ammonium chloride, octadecyldimethyl(3-triisopropylsilylpropyl)ammonium chloride, heptadecyldimethyl(3-trimethoxylsilylpropyl)ammonium chloride, heptadecyldiisopropyl(2-triethoxysilylethyl)ammonium chloride, hexadecyldimethyl(3-trimethoxysilylpropyl)ammonium chloride, hexadecyldimethyl(3-trimethoxysilylpropyl)ammonium acetate, and pentadecyldimethyl(3-triethoxysilylpropyl)ammonium chloride.

In yet another preferable example of the method of fixing an antibacterial agent of the present invention, it is preferable that the cationic surfactant (b1) is a cationic surfactant (b11) represented by general formula (2) below.

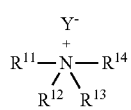

(2)

In general formula (2), $R^{11}$ represents a hydrocarbon group having 6 or more carbon atoms, $R^{12}$, $R^{13}$ and $R^{14}$ represent lower hydrocarbon groups, respectively, which may be the same or different from each other, and Y represents a halogen ion or an organic carbonyloxy ion.

In yet another preferable example of the method of fixing an antibacterial agent of the present invention, it is acceptable that $R^{11}$ of the cationic surfactant (b11) represented by general formula (2) above represents a $C_{10-25}$ alkyl group, $R^{12}$, $R^{13}$ and $R^{14}$ represent $C_{1-6}$ lower alkyl groups, respectively, which alkyl groups may be the same or different from each other, and Y represents a halogen ion or an organic carbonyloxy ion.

In yet another preferable example of the method of fixing an antibacterial agent of the present invention, it is preferable that the cationic surfactant (b11) is at least one type of compound selected from the group consisting of hexadecyltrimethylammonium chloride, decyltrimethylammonium chloride, decyltriethylammonium acetate, dodecyltrimethylammonium acetate, dodecyltriisopropylammonium bromide, tridecyltriethylammonium bromide, tetradecyltrimethylammonium chloride, tetradecyltriethylammonium chloride, tetradecyltri-n-propylammonium chloride, pentadecyltrimethylammonium chloride, pentadecyltriethylammonium chloride, pentadecyltri-n-propylammonium chloride, hexadecyltriethylammonium chloride, hexadecyltri-n-propylammonium chloride, octadecyltrimethylammonium chloride, octadecyltriethylammonium chloride, and octadecyltri-n-propylammonium chloride.

In yet another preferable example of the method of fixing an antibacterial agent of the present invention, it is acceptable that the cationic surfactant (1) is N-cocoyl-alginine ethyl ester pyridone carboxylate salt (b12) or cetylpyridinium salt (b13).

In yet another preferable example of the method of fixing an antibacterial agent of the present invention, it is preferable that the non-ionic surfactant (b2) is at least one type of non-ionic surfactant selected from the group consisting of alkyl ethers or esters of fatty acids derived from polyoxyalkylene glycol containing polyoxyethylene unit and/or polyoxypropylene unit, sorbitan esters of fatty acids, fatty acid monoglyceride, esters of fatty acids, fatty acid alkanolamides, fatty acid amides, alkyl ethers, alkyl amine oxides, polyoxyethylenealkyl ethers, and polyoxyethylene nonylphenyl ether.

In yet another preferable example of the method of fixing an antibacterial agent of the present invention, the non-ionic surfactant (b2) is preferably polyoxyethylene sorbitan monolaurate.

In yet another preferable example of the method of fixing an antibacterial agent of the present invention, it is preferable that the amphoteric surfactant (b3) is at least one type of compound selected from the group consisting of betaine-based compounds and amine oxide-based compounds.

In yet another preferable example of the method of fixing an antibacterial agent of the present invention, the amphoteric ionic surfactant (b3) is preferably lauramide propyl dimethylamine oxide or lauryldimethylamine oxide.

An article of the present invention is characterized in that the article has an antibacterial agent on a surface thereof, the antibacterial agent being fixed on the surface by the aforementioned method of fixing an antibacterial agent.

Effect of the Invention

According to the present invention, a silicon-containing compound can be fixed on a synthetic resin-based article or the like, on which fixation of the silicon-containing compound was conventionally difficult, whereby there is obtained an advantageous effect that articles of a wide range of materials can be imparted with excellent antibacterial property and good persistence of antibacterial activity.

BRIEF DESCRIPTION OF THE DRAWINGS

The patent or application file contains at least one drawing executed in color. Copies of this patent or patent application publication with color drawings will be provided by the Office upon request and payment of the necessary fee.

BEST MODE FOR IMPLEMENTING THE INVENTION

Figure 1:
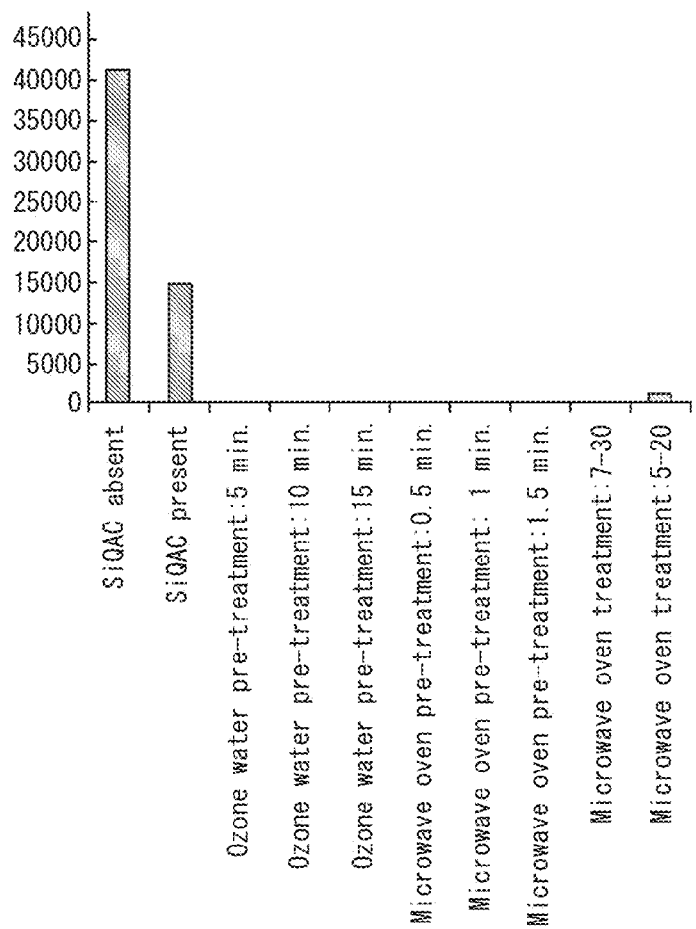
FIG. 1 is a graph making comparison of antibacterial performance of test pieces subjected to, in addition to a treatment of fixing an antibacterial agent thereon, ozone water treatment or 1-10 GHz microwave irradiation treatment, a test piece subjected to only the treatment of fixing an antibacterial agent thereon, and a test piece subjected to no treatments.

The present invention will be described in detail hereinafter. The method of fixing an antibacterial agent of the present invention characteristically has the steps of: subjecting a surface of an article to a surface treatment of providing the surface with oxygen-containing functional groups; and then subjecting the article to a treatment using an antibacterial agent composition including a silicon-containing compound (a) represented by general formula (1) below.

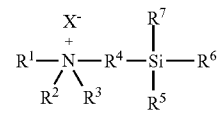

In general formula (1), $R^1$ represents a hydrocarbon group having 6 or more carbon atoms, $R^2$ and $R^3$ represent lower hydrocarbon groups, respectively, which hydrocarbon groups may be the same or different from each other, $R^4$ represents a divalent lower hydrocarbon group, $R^5$, $R^6$ and $R^7$ represent lower alkyl groups or lower alkoxy groups, respectively, which may be the same or different from each other, and X represents a halogen ion or an organic carbonyloxy ion. Regarding the aforementioned surface treatment, it suffices that the surface treatment is a treatment of providing a surface of an article with oxygen-containing functional groups such as —O or —OH and specific examples of a preferable surface treatment include ozone water treatment and 1-10 GHz microwave irradiation treatment. It should be noted that, in the method of fixing an antibacterial agent according to the present invention, it is acceptable to first treat a subject article by using the antibacterial agent composition and then subject the article to a surface treatment by irradiating a surface of the article with 1-10 GHz microwave in a state where the antibacterial agent composition remains on the surface of the article. The same effect can be obtained by this modified version of the method.

As described above, each of the method of subjecting a surface of an article to a surface treatment of providing the surface with oxygen-containing functional groups by ozone water treatment or 1-10 GHz microwave irradiation treatment and then treating the article with an antibacterial agent composition, and the method of applying the antibacterial agent composition by coating to a surface of an article and then subjecting the article to 1-10 GHz microwave irradiation treatment in a state where the antibacterial agent composition remains on the surface of the article, facilitates bonding of the silicon-containing compound as an antibacterial component included in the antibacterial agent composition to the surface of the article and a film of the silicon-containing compound is satisfactorily formed on the surface of the article, whereby the article can be imparted with excellent antibacterial property and good persistence of such antibacterial activity.

The treatment by using ozone water is not subjected to any particular restriction and can be carried out by bringing a surface of an article into contact with ozone water by, for example, immersing the article in ozone water of which ozone concentration has been appropriately adjusted, or spraying ozone water onto the article, or coating the article with ozone water. The processing time by ozone water can be appropriately changed in accordance with a concentration of ozone water to be used. For example, in a case where the ozone concentration is 0.4 to 0.6 ppm, an immersion treatment for approximately 5 minutes suffices. In a case where the ozone concentration is within a standard range of a few ppm, simply spraying the ozone water on an article and leaving the article so that it dries naturally suffices to impart the article with satisfactory antibacterial property and good persistence of antibacterial activity.

It is assumed that treating an article with ozone water by the method as described above radicalizes hydrogen portions of hydrocarbon, thereby generating oxygen-containing functional groups (—OH or —CHO) and providing a surface of an article with these oxygen-containing functional groups, so that reactivity of the surface of the article with the antibacterial component in the antibacterial agent composition is enhanced and the article is imparted with excellent antibacterial property and enhanced persistence of antibacterial activity.

The 1-10 GHz microwave irradiation treatment described above is not subjected to any particular restriction. The microwave irradiation is preferably a treatment by using a microwave oven and can be carried out by setting an article within a microwave oven and irradiating the article with microwave by the microwave oven. In the present embodiment, "a microwave oven" represents a cooking device for heating food by irradiating the food with high frequency electromagnetic wave and may be any of devices for heating food by irradiating the food with microwave typically having a wavelength of 2.450 GHz. Regarding an irradiation method of microwave, either batch-type microwave irradiation or continuous-type microwave irradiation is acceptable. Examples of the microwave oven which can be used in the present invention include a microwave oven for home use, a microwave oven having high output for business use, a microwave acceleration device for industrial use, and the like. Regarding the output and the processing time by a microwave oven, a sufficient effect can be obtained by a treatment with output: 700 W and processing time: 30 seconds in a case where the microwave irradiation treatment is carried out prior to the treatment with the antibacterial agent composition, and a sufficient effect can be obtained by a treatment with output: 700 W and processing time: 20 seconds or output: 500 W and processing time: 30 seconds in a case where the microwave irradiation treatment is carried out after the treatment with the antibacterial agent composition. Specifically, irradiation of an article with microwave excites atoms and/or breaks CH bonding at a surface of an article, whereby the excited atoms and/or the broken CH bonding are reacted with oxygen in the atmosphere to form oxygen-containing functional groups. Oxygen-containing functional groups are generated by irradiating a surface of an article with microwave in such a manner as described above.

Each of the ozone water treatment and the 1-10 GHz microwave irradiation treatment can obtain the effect of the present invention. In the case of the ozone water treatment, the treatment can be easily carried out if an article to be treated is relatively large, e.g. a bathtub, whereby it is easy, when the article as a product is produced in a production line in a factory, to incorporate into the production line the treatment of imparting the product with antibacterial property by using the method of fixing antibacterial agent of the present invention. In the case of the 1-10 GHz microwave irradiation treatment, a microwave oven can be used for the treatment, i.e. the effect of the present invention can be obtained by using a microwave oven for home use, whereby there is an advantage that the method of fixing antibacterial agent of the present invention can be easily carried out at home.

The components constituting the composition of antibacterial agent described above for use in the method of fixing antibacterial agent of the present invention will be described in detail hereinafter. The silicon-containing compound (a) as an antibacterial component included in the antibacterial agent composition is a silica-containing compound represented by general formula (1) below.

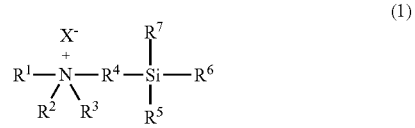

In general formula (1), $R^1$ represents a hydrocarbon group having 6 or more carbon atoms, $R^2$ and $R^3$ represent lower hydrocarbon groups, respectively, which hydrocarbon groups may be the same or different from each other, $R^4$ represents a divalent lower hydrocarbon group, $R^5$, $R^6$ and $R^7$ represent lower alkyl groups or lower alkoxy groups, respectively, which may be the same or different from each other, and X represents a halogen ion or an organic carbonyloxy ion (organic carboxylate ion). The antibacterial agent composition may include at least one type of silicon-containing compound represented by general formula (1).

Regarding the silicon-containing compound (a) represented by general formula (1), it is more preferable that $R^1$ thereof represents $C_{10-25}$ alkyl group, $R^2$ and $R^3$ represent $C_{1-6}$ lower alkyl groups, respectively, which alkyl groups may be the same or different from each other, $R^4$ represents a $C_{1-6}$ lower alkylene group, $R^5$, $R^6$ and $R^7$ represent $C_{1-6}$ lower alkyl groups or $C_{1-6}$ lower alkoxy groups, respectively, which may be the same or different from each other, and X represents a halogen ion or an organic carbonyloxy ion (organic carboxylate ion).

Examples of the hydrocarbon group having 6 or more carbon atoms of $R^1$ include hexyl, heptyl, octyl, nonyl, decyl, undecyl, dodecyl, tridecyl, tetradecyl, pentadecyl, hexadecyl, heptadecyl, octadecyl, nonadecyl, eicosyl, uneicosyl, doeicosyl, trieicosyl, tetraeicosyl, pentaeicosyl groups, and the like.

Examples of the lower hydrocarbon group which may be the same or different from each other of $R^2$, $R^3$ include methyl, ethyl, propyl, isopropyl, butyl, pentyl, hexyl, cyclohexyl, phenyl, tolyl groups, and the like.

Examples of the lower alkylene group of $R^4$ include methylene, ethylene, trimethylene, tetramethylene, hexamethylene groups.

Specific examples of the lower alkyl group or lower alkoxy group, which may be the same or different from each other, of $R^5$, $R^6$, $R^7$ include methoxy, ethoxy, propoxy, isopropoxy, butoxy, pentyloxy, hexyloxy, methyl, ethyl, propyl, isopropyl, butyl, pentyl, hexyl groups, and the like.

Examples of X include halogen ions such as chlorine ion, bromine ion, and organic carbonyloxy ions (organic carboxylate ions) such as methylcarbonyloxy ion (acetate ion), ethylcarbonyloxy ion (propionate ion), phenylcarbonyloxy ion (benzoate ion).

Specific examples of the silicon-containing compound (a) include octadecyldimethyl(3-trimethoxysilylpropyl)ammonium chloride, octadecyldimethyl(3-triethoxysilylpropyl) ammonium chloride, octadecyldiethyl(3-trimethoxysilylpropyl)ammonium chloride, octadecyldimethyl(3-trimethylsilylethyl)ammonium chloride, octadecyldipropyl (4-trimethoxysilylbutyl)ammonium acetate, octadecyldimethyl(3-triisopropoxysilylpropyl)ammonium chloride, octadecyldimethyl(3-triethylsilylpropyl)ammonium chloride, octadecyldimethyl(3-triisopropylsilylpropyl) ammonium chloride, heptadecyldimethyl(3-trimethoxysilylpropyl)ammonium chloride, heptadecyldiisopropyl(2-triethoxysilylethyl)ammonium chloride, hexadecyldimethyl (3-trimethoxysilylpropyl)ammonium chloride, hexadecyldimethyl(3-trimethoxysilylpropyl)ammonium acetate, and pentadecyldimethyl(3-triethoxysilylpropyl)ammonium chloride.

The composition of antibacterial agent may include at least one type of surfactant selected from the group consisting of: (b1) cationic surfactant (note that the aforementioned silicon compound is to be excluded); (b2) non-ionic surfactant; and (b3) amphoteric surfactant.

The cationic surfactant (b1) is a cationic surfactant represented by general formula (2) below. Specifically, the cationic surfactant (b1) is a cationic surfactant (b11) other than the aforementioned silicon-containing compound (a).

(2)

In general formula (2), $R^{11}$ represents a hydrocarbon group having 6 or more carbon atoms, $R^{12}$, $R^{13}$ and $R^{14}$ represent lower hydrocarbon groups, respectively, which may be the same or different from each other. The cationic surfactant (b1) is preferably N-cocoyl-alginine ethyl ester pyridone carboxylate salt (b12) or cetylpyridinium salt (b13) such as cetylpyridinium chloride.

Further, regarding the cationic surfactant (b11) represented by general formula (2), it is preferable that $R^{11}$ represents a $C_{10-25}$ alkyl group, $R^{12}$, $R^{13}$ and $R^{14}$ represent $C_{1-6}$ lower alkyl groups, respectively, which alkyl groups may be the same or different from each other, and Y represents a halogen ion or an organic carbonyloxy ion (organic carboxylate ion).

Examples of the hydrocarbon group $R^H$ having 6 or more carbon atoms of the cationic surfactant (b11) represented by general formula (2) include the hydrocarbon groups having 6 or more carbon atoms exemplified as $R^1$ of general formula (1) of the silicon-containing compound (a).

Examples of $R^{12}$, $R^{13}$ and $R^{14}$ of the cationic surfactant (b11) represented by general formula (2) include the lower hydrocarbon groups exemplified as $R^2$ and $R^3$ of general formula (1) of the silicon-containing compound (a).

Specific examples of the cationic surfactant (b11) represented by general formula (2) include hexadecyltrimethylammonium chloride, decyltrimethylammonium chloride, decyltriethylammonium acetate, dodecyltrimethylammonium acetate, dodecyltriisopropylammonium bromide, tridecyltriethylammonium bromide, tetradecyltrimethylammonium chloride, tetradecyltriethylammonium chloride, tetradecyltri-n-propylammonium chloride, pentadecyltrimethylammonium chloride, pentadecyltriethylammonium chloride, pentadecyltri-n-propylammonium chloride, hexadecyltriethylammonium chloride, hexadecyltri-n-propylammonium chloride, octadecyltrimethylammonium chloride, octaclecyltriethylammonium chloride, and octadecyltri-n-propylammonium chloride. Among these examples, hexadecyltrimethylammonium chloride is the most preferable.

The non-ionic surfactant (b2) is at least one type of non-ionic surfactant selected from the group consisting of alkyl ethers or esters of fatty acids derived from polyoxyalkylene glycol containing polyoxyethylene unit and/or polyoxypropylene unit, sorbitan esters of fatty acids, fatty acid monoglyceride, fatty acid alkanolamides, fatty acid amides, alkyl ethers, alkyl amine oxides, polyoxyethylenealkyl ethers, and polyoxyethylene nonylphenyl ether.

Specific examples of the non-ionic surfactant (b2) include at least one type of non-ionic surfactant selected from the group consisting of monoalkyl ether of polyethylene glycol, monoalkyl ether of polyalkylene glycol having both polyoxyethylene unit and polyoxypropylene unit, sorbitan laurylate, polyoxyethylene sorbitan monolaurate, fatty acid monoglyceride, fatty acid esters, fatty acid alkanolamides, fatty acid amides, alkyl ethers, alkyl amine oxides, polyoxyethylenealkyl ethers, and polyoxyethylene nonylphenyl ether.

More specific examples of the non-ionic surfactant include: sorbitan ester of fatty acid such as sorbitan monolaurate, sorbitan sesquiisostearate; glycerin fatty acid ester such as glycerin monooleate, glycerin monoisostearate; polyglycerin fatty acid ester such as diglyceryl monooleate, decaglyceryl diisostearate; polyoxyethylene sorbitan esters of fatty acids such as polyoxyethylene sorbitan monooleate, polyoxyethylene sorbitan monooleate; polyoxyethylene sorbit ester of fatty acid such as polyoxyethylene sorbit monolaurate, polyoxyethylene sorbit tetraoleate; polyoxyethylene glycerin fatty acid ester such as polyoxyethylene griceryl monooleate, polyoxyethylene griceryl monooleate; polyoxyethylene glycol fatty acid ester such as polyoxyethylene monoisostearate, polyoxyethylene monooleate; polyethylene glycol difatty acid ester such as polyoxyethylene diisostearate, polyoxyethylene diisostearate; polyoxyethylene alkyl ether such as polyoxyethylene oleyl ether, polyoxyethylene oleyl ether (10 E.O.); polyoxyethelene polyoxypropylene alkyl ether, and the like. Among these examples, polyoxyethylene sorbitan monolaurate is the most preferable.

The amphoteric surfactant (b3) may be at least one type of compound selected from the group consisting of betaine-based compounds and amine oxide-based compounds.

Specifically, preferable examples of the betaine-based amphoteric surfactant include coco fatty acid amidopropyl carboxy betaine, lauryl dimethylamino acetic acid betaine, and imidazolium betaine. Among these examples, coco fatty acid amidopropyl carboxy betaine and lauryl dimethylamino acetic acid betaine are preferable in terms of stability of the silicon-containing compound as the antibacterial component of a solution.

Examples of the amine oxide-based amphoteric surfactant include lauramide propyl dimethylamine oxide, lauryldimethylamine oxide, and the like. Among these examples, lauramide propyl dimethylamine oxide, lauryldimethylamine oxide described above are preferable in terms of stability of the silicon-containing compound as the antibacterial component of a solution. Lauramide propyl dimethylamine oxide is the most preferable among the aforementioned betaine-based and amine oxide-based amphoteric surfactants in terms of long-term stability of the silicon-containing compound as the antibacterial component of a solution.

An aqueous solution is normally employed as a solvent of the antibacterial agent composition for use in the present invention. A mixed solvent of water and a hydrophilic solvent such as methanol, ethanol, propanol, acetone and the like can be used as long as the silicon-containing compound (a), the cationic surfactant (b1), and/or non-ionic surfactant (b2) and/or the amphoteric surfactant (b3) are soluble to the mixed solvent.

In a case where the antibacterial agent composition includes only the silicon-containing compound (a) as an effective component thereof, the content of the silicon-containing compound (a) in the antibacterial agent composition is generally in the range of 0.01 to 60 vol. % and preferably in the range of 0.1 to 10 vol. %. The content of the silicon-containing compound (a) is preferably within the aforementioned ranges in terms of sufficiently demonstrating the antibacterial effect and good persistence of the antibacterial activity.

In a case where the antibacterial agent composition includes (a) the silicon-containing compound and (b) at least one type of surfactant selected from the group consisting of cationic surfactant (note that the aforementioned silicon compound is to be excluded); non-ionic surfactant; and amphoteric surfactant as an effective component thereof, the content of the silicon-containing compound (a) in the antibacterial agent composition is generally in the range of 0.01 to 40 vol. % and preferably in the range of 0.1 to 10 vol. %, and the content of the surfactant (b) in the antibacterial agent composition is generally in the range of 0.007 to 20 vol. % and preferably in the range of 0.05 to 10 vol. %. The contents of the silicon-containing compound (a) and the surfactant (b) are preferably within the aforementioned ranges in terms of sufficiently demonstrating the cleaning effect, the antibacterial effect and good persistence of these effects.

An article can be treated with the antibacterial agent composition, either prior or after the ozone water treatment or the like, by any of immersing the article in the antibacterial agent composition, spraying the composition onto a surface of the article, coating a surface of the article with the composition, rinsing (washing) a surface of the article with the antibacterial agent composition several times, or wiping a surface of the article with a cloth soaked with the antibacterial agent composition. The method of treating a surface of the article with the antibacterial agent composition is not particularly restricted as long as an article can be brought into contact with the antibacterial agent composition for a predetermined time. Time duration for this treatment of fixing an antibacterial composition on a surface of an article may also be appropriately selected as long as the time is long enough to allow the antibacterial component included in the antibacterial agent composition to be sufficiently reacted with the surface of the article. In a case where a surface of an article is treated with the antibacterial agent composition after the surface treatment of providing the surface with oxygen-containing functional groups by the ozone water treatment or the 1-10 GHz microwave irradiation treatment, the antibacterial agent composition may be removed from the surface of the article according to necessity, by washing the surface with water or the like, after the treatment with the antibacterial agent composition. In a case where the 1-10 GHz microwave irradiation treatment is carried out after the treatment with the antibacterial agent composition, the antibacterial agent composition may be removed from the surface of the article according to necessity, by washing the surface with water or the like, after the microwave irradiation treatment.

Examples of an article where an antibacterial agent can be fixed on a surface thereof by the method of fixing antibacterial agent of the present invention include a wide variety of articles like dental materials such as implant, crown, bridge, orthodontic bracket, dental wire and the like, and tableware, eyeglasses, sinks, kitchen fixtures, toilets, toilet fixtures, bathtubs, bath-room fixtures, washbowls, washroom fixtures, textile products and clothes. The articles which have been treated by the method of fixing antibacterial agent of the present invention exhibit, even in a case where they are made of synthetic resin to which the antibacterial silicon-containing compound included in the antibacterial agent composition is not easily bonded, very good antibacterial property and good persistence of antibacterial activity. The type of material constituting the article is not particularly restricted. A variety of materials such as glass, porcelain, ceramics, metal, synthetic resin and the like can be imparted with good antibacterial property and good persistence of antibacterial activity by the method of fixing antibacterial agent of the present invention.

The present invention will be described further in detail by Examples hereinafter. The present invention is not restricted to these Examples.

EXAMPLES

Example 1

In the present Example, it was investigated how antibacterial property and persistence of antibacterial activity of an article having an antibacterial agent fixed thereon is affected by conducting a pretreatment with ozone water or microwave irradiation (a microwave oven) prior to carrying out the antibacterial agent fixing treatment using an antibacterial agent composition.

(Material)

A test piece of 10×10×0.2 mm acryl plate was used as an article on which an antibacterial agent was fixed. A strain GDH18 of *Candida Albicans* was used as the bacteria for the antibacterial property test. The bacteria was incubated on Sabouraud agar for 18 hours and then a bacteria solution having bacteria concentration of $1 \times 10^6$ cells/mL was prepared using ultra pure water (MQ water).

(Ozone Water Treatment)

Test pieces as 1×1 cm acryl plates were immersed for 5, 10, 15 minutes, respectively, in approximately 30 mL of ozone water (0.4 to 0.6 ppm) produced by "Ozone Dash" manufactured by Ozone Total System Co., Ltd. Each of the test pieces was then drained on a filtering paper, immersed in an aqueous solution as a mixture of octadecyldimethyl(3-trimethoxysilylpropyl)ammonium chloride (Si-QAC: 3% (vol./vol.)) and polyoxyethylene sorbitan monolaurate (PO: 1% (vol./vol.)), and washed with water, whereby the test pieces for the antibacterial test were obtained.

(Microwave Irradiation Treatment: Microwave Treatment 1)

Test pieces as 1×1 cm acryl plates were treated for 30, 60, 90 seconds, respectively, by using a microwave oven for home use (the product name "NE-EZ2" output: 700 W, microwave: 2.450 GHz, manufactured by Panasonic Corporation). Each test piece was then immediately immersed in an aqueous solution as a mixture of Si-QAC (3% (vol./vol.)) and PO (1% (vol./vol.)) and washed with water, whereby test pieces for the antibacterial test were obtained.

(Microwave Irradiation Treatment: Microwave Treatment 2)

Test pieces as 1×1 cm acryl plates were first immersed in a mixed aqueous solution of Si-QAC (3% (vol./vol.)) and lauramide propyl dimethylamine oxide (LAO) (1% (vol./vol.)) and then immediately treated by a microwave oven (700 W) for home use for 30 seconds and a microwave oven (500 W) for home use for 20 seconds. The acryl plate was then immediately washed with water, whereby test pieces for the antibacterial-property test were obtained.

(Antibacterial-Property Test)

A stock solution of *Candida albicans*, of which bacteria concentration had been adjusted in advance to be $1 \times 10^6$ cells/mL, was planted on a surface of each test piece obtained as described above by 25 μL, (2500 cells) for each piece. Each test piece was left for 2 hours to wait for sedimentation of the bacteria. Thereafter, 1 mL of Sabouraud agar containing chlorophenol red as a pH indicator (*Candida* yellow agar, manufactured by Fuji Pharma Co., Ltd.) was added to each test piece and the respective test pieces were incubated for 48 hours at 37° C. Next, ATP was extracted from the bacteria which grew on a surface of each test piece and quantitatively analyzed. Extraction of ATP was effected by immersing each test piece for 30 minutes in 500 μL of ATP extraction reagent "AF-2K1" for microorganism manufactured by DKK-TOA CORPORATION. The measurement of a quantity of ATP was carried out by setting the extraction solution thus obtained in a cell timer glow manufactured by Promega Corporation (formerly Tuner Biosystems).

The results of the antibacterial-property test are shown in FIG. 1. In the antibacterial-property test, a test piece subjected to neither the ozone water treatment nor the treatment with the Si-QAC (1% (vol./vol.) PO) solution and a test piece subjected to only the Si-QAC solution treatment were used as the controls.

The Y-axis of the graph shown in FIG. 1 represents the ATP quantity (pmol) per one sample, and 1 pmol of ATP corresponds to approximately 100 cells of the bacteria. Referring to the results of the antibacterial-property test, the number of the bacteria increased to $4 \times 10^6$ in the test piece subjected to neither the ozone water treatment nor the Si-QAC solution treatment (see "Si-QAC absent" in FIG. 1), while increase in the number of bacteria cells was curbed to approximately ⅓ in the test piece subjected to only the Si-QAC solution treatment and not to the ozone water treatment (see "Si-QAC present" in FIG. 1). In contrast, increase in the number of bacteria cells was more significantly curbed in the test pieces also subjected to the pretreatment than the test piece subjected to only the Si-QAC solution treatment and not to the ozone water treatment. More specifically, there was observed no growth of the bacteria in the cases where the ozone water treatment was carried out for more than 5 minutes and the cases where the microwave oven treatment was carried out for more than 0.5 minute.

Regarding the cases where the microwave oven treatment was carried out after the treatment with the Si-QAC solution, there was observed no growth of the bacteria in the test piece immersed in the (Si-QAC+LAO) solution and then subjected to microwave irradiation at 700 W for 30 seconds (see "Microwave oven treatment: 7-30" in FIG. 1). Although there was observed some growth of the bacteria in the test piece immersed in the (Si-QAC+LAO) solution and then subjected to microwave irradiation at 500 W for 20 seconds, this test piece exhibited a more than ten times better antibacterial effect than the test piece subjected to neither the ozone water treatment nor the Si-QAC solution treatment or the test piece subjected to only the Si-QAC solution treatment.

Example 2

In the present Example, the relationship between duration of the ozone water pretreatment and antibacterial performance and persistence of antibacterial activity in an article having an antibacterial agent fixed thereon was analyzed.

(Material)
Test pieces each having a dimension of 10×10×0.2 mm were prepared using acrylic resin for denture base (the product name "Acron MC", manufactured by GC Corporation), which acrylic resin was polymerized according to the conventional manner. A surface firmly attached on glass, of the test piece, was used as a test surface. A strain GDH18 of *Candida Albicans* was used as the bacteria for use in the antibacterial property test. The bacteria was incubated on Sabouraud agar for 18 hours and a bacteria solution having bacteria concentration of $1 \times 10^6$ cells/mL was prepared using ultra pure water (MQ water).

(Ozone Water Treatment)
The test pieces were immersed for 0, 1, 3, 5, 10 minutes, respectively, in approximately 30 mL of ozone water (0.4 to 0.6 ppm) produced by "Ozone Dash" manufactured by Ozone Total System Co., Ltd. Each of the test pieces was then drained on a filtering paper, immersed in a mixed aqueous solution of Si-QAC (3% (vol./vol.)) and PO (1% (vol./vol.)), and washed with water, whereby the test pieces for the antibacterial test were obtained.

(Antibacterial-Property Test)
A bacterial suspension, of which bacteria concentration had been adjusted in advance to be $1 \times 10^6$ cells/mL, was planted on a surface of each test piece by 25 μL (2000 cells) for each piece. Each test piece was left for 2 hours to wait for sedimentation of the bacteria. Thereafter, 1 mL of Sabouraud agar containing chlorophenol red as a pH indicator (*Candida* yellow agar, manufactured by Fuji Pharma Co., Ltd.) was added to each test piece and the respective test pieces were incubated at 37° C. In a case where the number of bacteria cells is increasing, the color of the agar changes from red (pH 6.0) to a color in the range of orange (approximately pH 4.5) to yellow (approximately pH 3.0) because the pH of the agar then becomes a value in the range of 6.0-4.5-3.0. Antibacterial property was evaluated using change in color of the agar as an index. The results are shown in the photographs shown in FIGS. 2 to 5. In these photographs, the symbol "未" represents a control or untreated sample subjected to neither the pretreatment nor the Si-QAC solution treatment.

Figure 2:
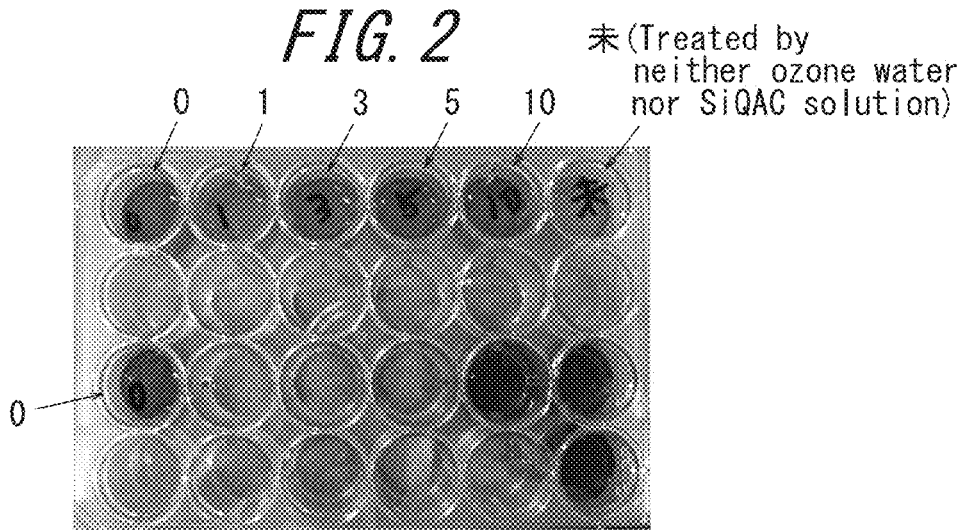
FIG. 2 is a view showing results obtained 12 hours after the start of incubation in an antibacterial property test in which test pieces were subjected to the antibacterial agent fixation treatment after being treated with ozone water for 0, 1, 3, 5, 10 minutes, respectively.

FIG. 2 shows the results obtained 12 hours after the start of the incubation. In FIG. 2, the agar of the untreated sample turned yellow, indicating that the number of bacteria cells therein increased to not less than $1 \times 10^8$ cells/mL, while the test pieces treated with ozone water for 0, 1, 3, 5, 10 minutes, respectively, and then the mixed solution of Si-QAC and PO exhibited no growth of the bacteria. Precisely, the sample treated with ozone water for 1 minute exhibited orange color, indicating that the number of bacteria cells therein increased in the order of $1 \times 10^5$ cells/mL.

Figure 3:
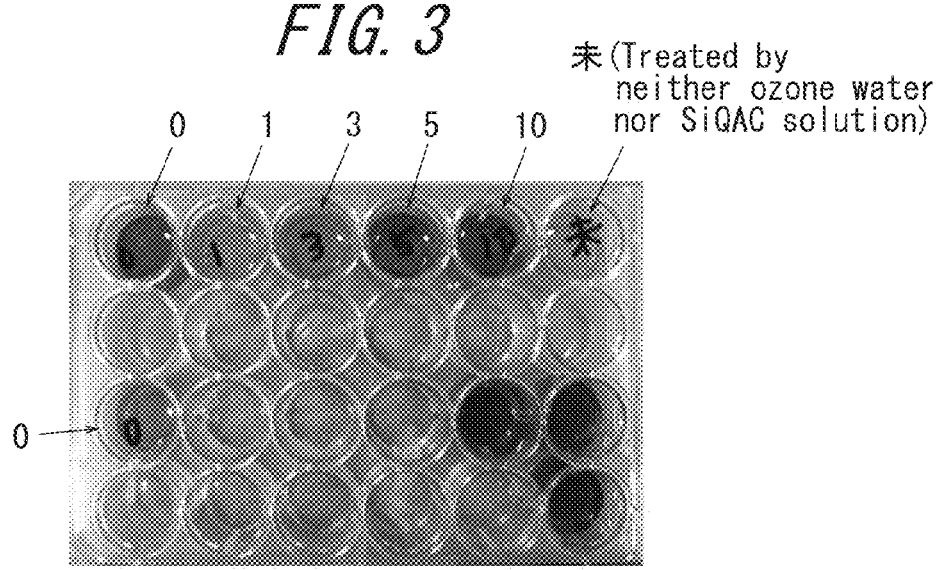
FIG. 3 is a view showing results obtained 18 hours after the start of incubation in the antibacterial property test in which test pieces were subjected to the antibacterial agent fixation treatment after being treated with ozone water for 0, 1, 3, 5, 10 minutes, respectively.
Figure 4:
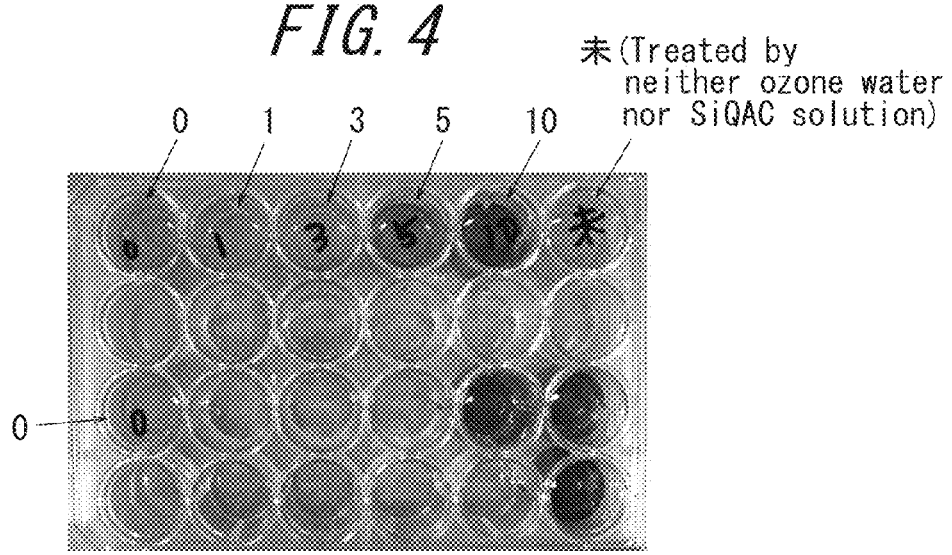
FIG. 4 is a view showing results obtained 36 hours after the start of incubation in the antibacterial property test in which test pieces were subjected to the antibacterial agent fixation treatment after being treated with ozone water for 0, 1, 3, 5, 10 minutes, respectively.

FIG. 3 and FIG. 4 each shows the results obtained 18-36 hours after the start of the incubation. As shown in FIGS. 3 and 4, the agars of the samples treated with ozone water for 0, 1, 3 minutes, respectively, turned yellow after 36 hours, indicating that the number of bacteria cells therein increased to not less than $1 \times 10^8$ cells/mL and that approximately 50-100 cells among the initially planted 2000 cells presumably survived after the treatments. In contrast, the test pieces treated with ozone water for 5, 10 minutes, respectively, and then the Si-QAC solution exhibited no growth of the bacteria after 18 hours. Regarding the test piece treated for ozone water for 5 minutes, it exhibited orange color after 36 hours, indicating that a few cells presumably survived after the treatments.

Figure 5:
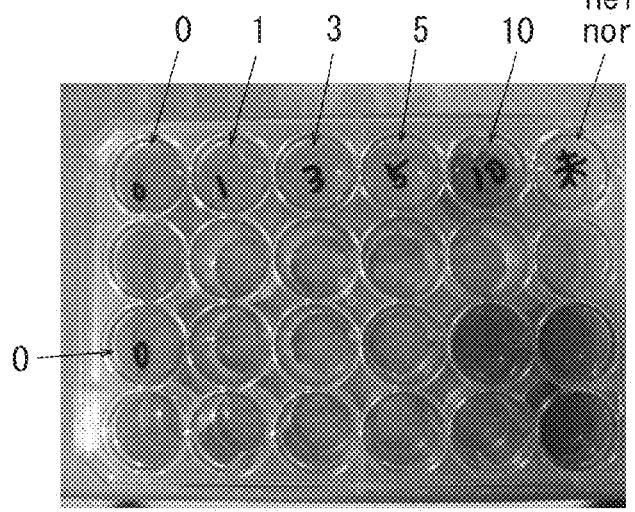
FIG. 5 is a view showing results obtained 48 hours after the start of incubation in the antibacterial property test in which test pieces were subjected to the antibacterial agent fixation treatment after being treated with ozone water for 0, 1, 3, 5, 10 minutes, respectively.
Figure 6:
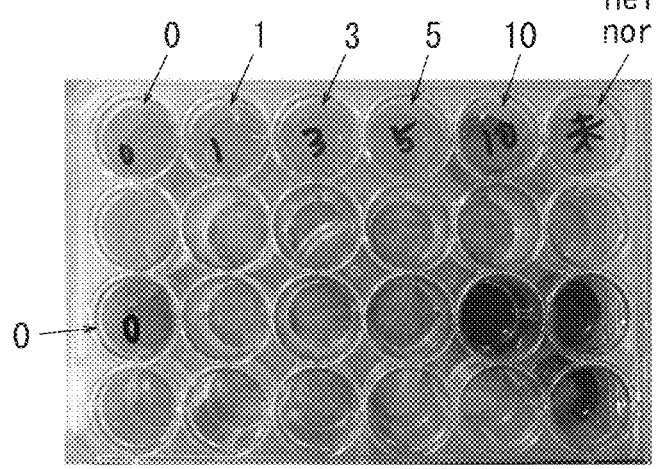
FIG. 6 is a view showing results obtained one week after the start of incubation in the antibacterial property test in which test pieces were subjected to the antibacterial agent fixation treatment after being treated with ozone water for 0, 1, 3, 5, 10 minutes, respectively.

FIG. 5 shows the results obtained 48 hours after the start of the incubation and FIG. 6 shows the results obtained one week after the start of the incubation. From FIG. 5 and FIG. 6, it is known that the states of the respective samples remained substantially unchanged between 48 hours and one week after the start of the incubation. As shown in FIG. 6, no growth of the bacteria was observed even one week after the start of the incubation and all of the planted bacterial was presumably killed in the test piece treated with ozone water for 10 minutes.

Example 3

In the present Example, it was investigated how the ozone water treatment and use of the antibacterial agent composition containing cationic surfactant or amphoteric surfactant affect antibacterial property and persistence of antibacterial activity of an article.

(Material)

A hemocytometer cover glass was used as a test piece of an article on which an antibacterial agent is fixed. A strain GDH18 of *Candida Albicans* was used as the bacteria for use in the antibacterial-property test. The bacteria was incubated on Sabouraud agar for 18 hours and a bacteria solution having bacteria concentration of $1 \times 10^6$ cells/mL was prepared using ultra pure water (MQ water).

(Ozone Water Treatment)

The test pieces were immersed for 1 minute in approximately 30 mL of ozone water (0.4 to 0.6 ppm) produced by using ultra pure water and "Ozone Dash" manufactured by Ozone Total System Co., Ltd. The test pieces were then drained on a filtering paper and immersed for 5 minutes in following aqueous solutions, respectively:

1) a mixed aqueous solution of octadecyldimethyl(3-triethoxysilylpropyl)ammonium chloride (EtAC) (3% (vol./vol.)) and LAO (1% (vol./vol.));

2) a mixed aqueous solution of EtAC (3% (vol./vol.)) and lauryldimethylamine oxide (Aromox) (1% (vol./vol.));

3) a mixed aqueous solution of EtAC (3% (vol./vol.)) and hexadecyltrimethylammonium chloride (HD) (1% (vol./vol.));

4) a mixed aqueous solution of EtAC (3% (vol./vol.)) and cetylpyridinium chloride (CPC) (1% (vol./vol.));

5) 70% ethanol solution of EtAC (3% (vol./vol.));

6) an aqueous solution of EtAC (3% (vol./vol.)).

Each test piece was then taken out of the aqueous solution, immediately washed with water such that excess antibacterial composition was removed, whereby test pieces for the antibacterial-property test were obtained.

A test piece immersed in ultra pure water and then 5) 70% ethanol solution of EtAC (3% (vol./vol.)) for 5 minutes and another test piece immersed only in ultra pure water were prepared as two types of control.

A bacterial suspension, of which bacteria concentration had been adjusted in advance to be $1 \times 10^6$ cells/mL, was planted on a surface of each test piece by 50 μL (approximately 5000 cells) for each piece. Each test piece was left for 2 hours at the room temperature to wait for sedimentation of the bacteria. Thereafter, 5 mL of Sabouraud agar containing chlorophenol red as a pH indicator (*Candida* yellow agar, manufactured by Fuji Pharma Co., Ltd.) was added to each test piece and the respective test pieces were continually incubated at 37° C. In a case where the number of bacteria cells is increasing, the color of the agar changes from red (pH 6.0) to a color in the range of orange (approximately pH 4.5, the number of bacteria cells: $1 \times 10^7$ cells/mL or more) to yellow (approximately pH 3.0, the number of bacteria cells: $1 \times 10^8$ cells/mL or more) because the pH of the agar then becomes a value in the range of 6.0-4.5-3.0. Antibacterial property was evaluated using such change in color as described above of the agar as an index.

The agar of each condition 1)-6) exhibited red color 24 hours after the start of the incubation, indicating that growth of bacteria can be sufficiently suppressed for 24 hours after planting of the bacteria by an antibacterial agent fixing treatment using any of the aforementioned solutions 1)-6). The agar of the test piece as the control not subjected to the antibacterial agent fixing treatment (the test piece immersed only in ultra pure water) slightly turned orange.

Figure 7:
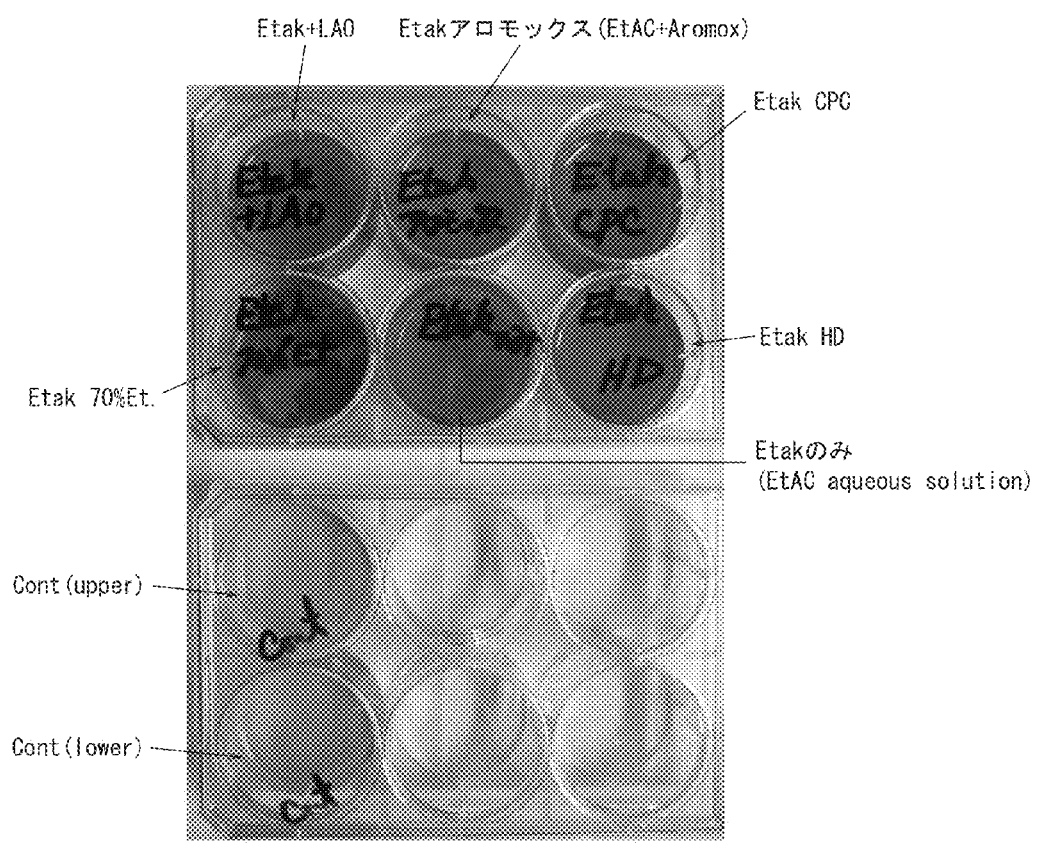
FIG. 7 is a view showing results obtained 33 hours after the start of incubation in an antibacterial property test in which test pieces were subjected to the antibacterial agent fixation treatment by using respective solutions in Example 3.

The results obtained 33 hours after the start of the incubation are shown in FIG. 7. The symbols representing the respective solutions and the controls in FIG. 7 (and FIG. 8 described later) are tabulated in TABLE 1 below.

TABLE 1

Figure 8:
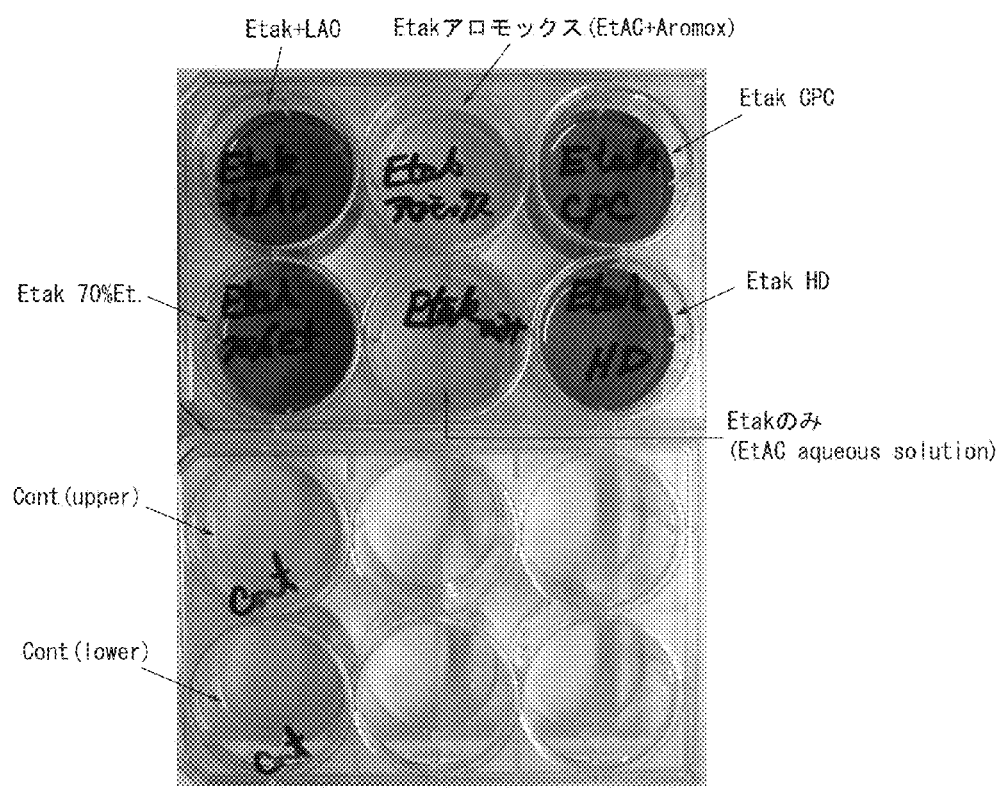
FIG. 8 is a view showing results obtained 45 hours after the start of incubation in an antibacterial property test in which test pieces were subjected to the antibacterial agent fixation treatment by using respective solutions in Example 3.

| | Type of respective solutions | Symbols in FIGS. 7 and 8 |
|---|---|---|
| 1) | EtAC + LAO | "Etak + LAO" |
| 2) | EtAC + Aromax | "Etakアロモックス" |
| 3) | EtAC + HD | "Etak HD" |
| 4) | EtAC + CPC | "Etak CPC" |
| 5) | 70% ethanol solution of EtAC | "Etak 70% Et." |
| 6) | EtAC aqueous solution | "Etakのみ" |
| Control | EtAC treatment after immersion in ultra pure water | "Cont" (upper) |
| Control | Immersion in ultra pure water only | "Cont" (lower) |

(Note:
"Etak" represents EtAC)

In Example 3, it is assumed that the controls hardly exhibited antibacterial performance because they were not subjected to the ozone water treatment and the duration of the EtAC treatment was very short (5 minutes).

Among the samples subjected to the ozone water treatment (1 minute) in advance, 1) EtAC+LAO; 3) EtAC+HD; 4) EtAC+CPC; and 5) 70% ethanol solution of EtAC samples exhibited as a result of the antibacterial agent fixing treatment therein no growth of bacteria on a glass surface, indicating very good antibacterial property. In contrast, the samples of 6) EtAC only and 2) EtAC+Aromox, although these samples had been subjected to the ozone water treatment, exhibited a slightly poor antibacterial performance than the samples of 1), 3), 4) and 5), indicating an increase in the number of bacteria cells to $0.5 \times 10^7$/mL or so for 33 hours.

The results obtained 45 hours after the start of the incubation are shown in FIG. 8. The symbols representing the respective solutions and the controls in FIG. 8 are the same as those of FIG. 7 shown in TABLE 1. It is understood from FIG. 8 that the agars of the sample immersed in MQ water and then treated with Etak (i.e. the "upper" control) and the sample immersed only in MQ water (i.e. the "lower" control) turned strongly yellow, indicating that the number of bacteria cells therein had increased to $0.5 \times 10^8$/mL or more.

Among the samples subjected to the ozone water treatment (1 minute) in advance, 1) EtAC+LAO; 3) EtAC+HD; 4) EtAC+CPC; and 5) 70% ethanol solution of EtAC samples exhibited as a result of the antibacterial agent fixing treatment therein no growth of bacteria on a glass surface, indicating very good antibacterial property. In contrast, the samples of 6) EtAC only and 2) EtAC+Aromox, although these samples had been subjected to the ozone water treatment, exhibited a slightly poor antibacterial performance than the samples of 1), 3), 4) and 5), indicating an increase in the number of bacteria cells to $0.5 \times 10^8$/mL or more for 45 hours.

It should be noted that the results similar to those shown in FIG. 8 were obtained 78 hours after the start of the incubation.

The invention claimed is:

1. A method of fixing an antibacterial agent on an article, comprising the steps of:
    subjecting a surface of an article to an ozone water treatment of providing the surface with oxygen-containing functional groups by treating the surface with ozone water; and then
    subjecting the article to a treatment using an antibacterial agent composition including a silicon-containing compound represented by the general formula below

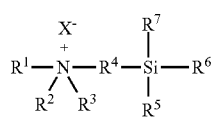

(1)

wherein $R^1$ represents a non-cyclic alkyl group having 6 to 25 carbon atoms, $R^2$ and $R^3$ represent $C_{1-6}$ hydrocarbon groups, respectively, which hydrocarbon groups may be the same or different from each other, $R^4$ represents a divalent $C_{1-6}$ hydrocarbon group, $R^5$, $R^6$ and $R^7$ represent $C_{1-6}$ alkoxy groups, respectively, which may be the same or different from each other, and X represents a halogen ion or an organic carbonyloxy ion; and wherein the antibacterial agent composition further comprises at least one non-ionic surfactant, and the article is made of an acrylic resin.

2. The method of fixing an antibacterial agent of claim 1, wherein said ozone water treatment is one of immersing the article in ozone water, spraying ozone water onto the article, or coating the article with ozone water.

3. The method of fixing an antibacterial agent of claim 1, wherein $R^1$ of the silicon-containing compound represented by general formula represents $C_{10-25}$ alkyl group, $R^2$ and $R^3$ represent $C_{1-6}$ alkyl groups, respectively, which alkyl groups may be the same or different from each other, $R^4$ represents a $C_{1-6}$ alkylene group, $R^5$, $R^6$ and $R^7$ represent $C_{1-6}$ alkoxy groups, respectively, which may be the same or different from each other, and X represents a halogen ion or an organic carbonyloxy ion.

4. The method of fixing an antibacterial agent of claim 1, wherein the silicon-containing compound represented by general formula is at least one type of silicon-containing compound selected from the group consisting of:
    octadecyldimethyl(3-trimethoxysilylpropyl)ammonium chloride,
    octadecyldimethyl(3-triethoxysilylpropyl)ammonium chloride,
    octadecyldiethyl(3-trimethoxysilylpropyl)ammonium chloride,
    octadecyldipropyl(4-trimethoxysilylbutyl)ammonium acetate,
    octadecyldimethyl(3-triisopropoxysilylpropyl)ammonium chloride,
    heptadecyldimethyl(3-trimethoxylsilylpropyl)ammonium chloride,
    heptadecyldiisopropyl(2-triethoxysilylethyl)ammonium chloride,
    hexadecyldimethyl(3-trimethoxysilylpropyl)ammonium chloride,
    hexadecyldimethyl(3-trimethoxysilylpropyl)ammonium acetate, and
    pentadecyldimethyl(3-triethoxysilylpropyl)ammonium chloride.

5. The method of fixing an antibacterial agent of claim 1, wherein the non-ionic surfactant is at least one type of non-ionic surfactant selected from the group consisting of alkyl ethers or esters of fatty acids derived from polyoxyalkylene glycol containing polyoxyethylene unit and/or polyoxypropylene unit, sorbitan esters of fatty acids, fatty acid monoglyceride, esters of fatty acids, fatty acid alkanolamides, fatty acid amides, alkyl ethers, alkyl amine oxides, polyoxyethylenealkyl ethers, and polyoxyethylene nonylphenyl ether.

6. The method of fixing an antibacterial agent of claim 5, wherein the non-ionic surfactant is polyoxyethylene sorbitan monolaurate.

* * * * *